(12) United States Patent
Burton, Jr. et al.

(10) Patent No.: US 8,679,451 B2
(45) Date of Patent: Mar. 25, 2014

(54) METHOD FOR MAKING ALUMINOSILICATE ZSM-12

(75) Inventors: Allen W. Burton, Jr., Richmond, CA (US); Tracy M. Davis, Pinole, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 91 days.

(21) Appl. No.: 12/622,680

(22) Filed: Nov. 20, 2009

(65) Prior Publication Data
US 2011/0123433 A1 May 26, 2011

(51) Int. Cl.
*C01B 33/36* (2006.01)
*C01B 39/00* (2006.01)

(52) U.S. Cl.
USPC .......................................... 423/704; 423/718

(58) Field of Classification Search
CPC .......... C01B 39/48; C01B 37/02; C07C 2/12; B01J 29/70; B01J 29/85
USPC .................................................. 423/700–718
See application file for complete search history.

(56) References Cited

U.S. PATENT DOCUMENTS

| | | | |
|---|---|---|---|
| 3,832,449 A | 8/1974 | Rosinski et al. | |
| 4,452,769 A | 6/1984 | Chu et al. | |
| 4,552,739 A | 11/1985 | Kuhl | |
| 5,282,958 A | 2/1994 | Santilli et al. | |
| 5,558,851 A | 9/1996 | Miller | |
| 5,785,947 A | 7/1998 | Zones et al. | |
| 5,800,801 A | 9/1998 | Tejada et al. | |
| 6,124,516 A | 9/2000 | Wu et al. | |
| 6,652,832 B2 | 11/2003 | Malek | |
| 6,893,624 B2 | 5/2005 | Lai et al. | |
| 7,390,763 B2 | 6/2008 | Zones et al. | |
| 7,468,126 B2 | 12/2008 | Zones et al. | |
| 7,550,073 B2 | 6/2009 | Zones et al. | |
| 2008/0035525 A1 | 2/2008 | Burgfels et al. | |

OTHER PUBLICATIONS

Zones, Stacy and Allen Burton, Diquaternary structure-directing agents built upon charged imidazolium ring centers and their use in synthesis of one-dimensional pore zeolites, 2005, J. Mater. Chem., 15, pp. 4215-4223.*
S.I. Zones and A.W. Burton "Diquaternary structure-directing agents built upon charged imidazolium ring centers and their use in synthesis of one-dimensional pore zeolites" J. Mater. Chem. 2005, 15, 4215-4223.
Supplementary European Search Report, EP10832231.4, completed Apr. 15, 2013.
K.S. Yoo, S. Gopal and P.G. Smirniotis "Enhancement of n-Hexane Cracking Activity over Modified ZSM-12 Zeolites" Ind. Eng. Chem. Res. 2005, 44, 4562-4568.

* cited by examiner

*Primary Examiner* — Bijay Saha
(74) *Attorney, Agent, or Firm* — Michael D. Ross; Terrence Flaherty

(57) ABSTRACT

An aluminosilicate ZSM-12 may be prepared de novo in a small crystalline form from a reaction mixture containing a source of silica and a source of alumina. A small crystalline form of aluminosilicate ZSM-12 may also be prepared from a small crystalline form of borosilicate ZSM-12 by replacement of boron in the borosilicate ZSM-12 framework with aluminum. The aluminosilicate ZSM-12 is useful as an isomerization selective catalyst in processes such as isomerization dewaxing hydrocarbon feedstocks.

12 Claims, 6 Drawing Sheets

ND FOR MAKING ALUMINOSILICATE ZSM-12

METHOD FOR MAKING ALUMINOSILICATE ZSM-12

FIELD OF THE INVENTION

The present invention relates to aluminosilicate ZSM-12 compositions, methods for directly and indirectly preparing aluminosilicate ZSM-12, and uses for ZSM-12.

BACKGROUND OF THE INVENTION

Molecular sieves are a class of important materials used in the chemical industry for processes such as gas stream purification and hydrocarbon conversion processes. Molecular sieves are porous solids having interconnected pores of different sizes. Molecular sieves typically have a one-, two- or three-dimensional crystalline pore structure having pores of one or more molecular dimensions that selectively adsorb molecules that can enter the pores, and exclude those molecules that are too large. The pore size, pore shape, interstitial spacing or channels, composition, crystal morphology and structure are a few characteristics of molecular sieves that determine their use in various hydrocarbon adsorption and conversion processes.

For the petroleum and petrochemical industries, the most commercially useful molecular sieves are known as zeolites. A zeolite is an aluminosilicate having an open framework structure formed from corner sharing the oxygen atoms of $[SiO_4]$ and $[AlO_4]$ tetrahedra or octahedra. Mobile extra framework cations reside in the pores for balancing charges along the zeolite framework. These charges are a result of substitution of a tetrahedral framework cation (e.g. $Si^{4+}$) with a trivalent or pentavalent cation. Extra framework cations counter-balance these charges preserving the electroneutrality of the framework, and these cations are exchangeable with other cations and/or protons.

Synthetic aluminosilicate molecular sieves, particularly zeolites, are typically synthesized by mixing sources of alumina and silica in an aqueous media, often in the presence of a structure directing agent or templating agent. The structure of the molecular sieve formed is determined in part by solubility of the various sources, silica-to-alumina ratio, nature of the cation, synthesis conditions (temperature, pressure, mixing agitation), order of addition, type of templating agent, and the like.

Molecular sieves identified by the International Zeolite Associate (IZA) as having the structure code MTW are known. ZSM-12 is a known crystalline MTW material, and is useful in many processes, including various catalytic reactions. Accordingly, there is a continued need for new methods for making ZSM-12, particularly small crystal forms of this material.

Further, there is a current need to identify molecular sieves that are suitable for catalystic n-paraffin isomerization. High-quality lubricating oils are required for the operation of modern machinery and automobiles. Most lubricating oil feedstocks must be dewaxed in order to produce high-quality lubricating oils. Catalytic dewaxing has advantages over solvent extraction of waxes, and the former is a valuable hydrocarbon processing technique. Catalytic dewaxing may be accomplished by cracking and/or isomerization of n-paraffins in the feedstocks.

Some prior art catalytic dewaxing processes operate at relatively high temperatures and pressures, resulting in extensive cracking and the production of lower value light gases. Therefore, catalytic dewaxing by isomerization of n-paraffins at lower temperatures is desirable. Accordingly, there is a continued need for new catalysts having improved hydrocarbon isomerization selectivity and conversion.

SUMMARY OF THE INVENTION

In accordance with the present invention there is provided an aluminosilicate ZSM-12 molecular sieve having a mole ratio of between 30 and 100 of silicon oxide to aluminum oxide and having, after calcination, the powder X-ray diffraction (XRD) lines of Table 5.

The aluminosilicate ZSM-12 is prepared by contacting under crystallization conditions: (1) at least one source of silicon oxide; (2) at least one source of aluminum oxide; (3) at least one source of an element selected from Groups 1 and 2 of the Periodic Table; (4) hydroxide ions; (5) 1,6-bis(2,3-dimethylimidazolium)hexane cations; and (6) optionally, a second nitrogen-containing structure directing agent suitable for synthesizing ZSM-12.

The aluminosilicate ZSM-12 synthesized per the teachings herein has a composition, as-synthesized and in the anhydrous state, in terms of mole ratios, as follows:

| | |
|---|---|
| $SiO_2/Al_2O_3$ | 30-100 |
| $(Q + A)/SiO_2$ | 0.015-0.06 |
| $M/SiO_2$ | 0-0.1 | wherein:

(1) M is at least one element selected from Groups 1 and 2 of the Periodic Table;

(2) Q is cationic 1,6-bis(2,3-dimethylimidazolium)hexane, and Q>0; and (3) A is a second nitrogen-containing structure directing agent, and A≥0.

According to a further aspect of the present invention there is provided a method of preparing aluminosilicate ZSM-12 by:

(a) preparing a reaction mixture containing: (1) at least one source of silicon oxide; (2) at least one source of boron oxide; (3) at least one source of an element selected from Groups 1 and 2 of the Periodic Table; (4) hydroxide ions; (5) cationic 1,4-bis(trimethylammonium)butane or cationic 1,4-bis(N-methylpiperidinium)butane as the structure directing agent; and (6) water;

b) maintaining the reaction mixture under crystallization conditions sufficient to form crystals of borosilicate ZSM-12; and c) replacing boron in the framework of the borosilicate ZSM-12 with aluminum to provide aluminosilicate ZSM-12.

The present invention also includes a process for converting a hydrocarbonaceous feed by contacting the feed under isomerization conditions with a ZSM-12 molecular sieve having a mole ratio of between 30 and 100 of silicon oxide to aluminum oxide and having, after calcination, the powder XRD lines of Table 5.

DETAILED DESCRIPTION OF THE INVENTION

Introduction

Figure 1:
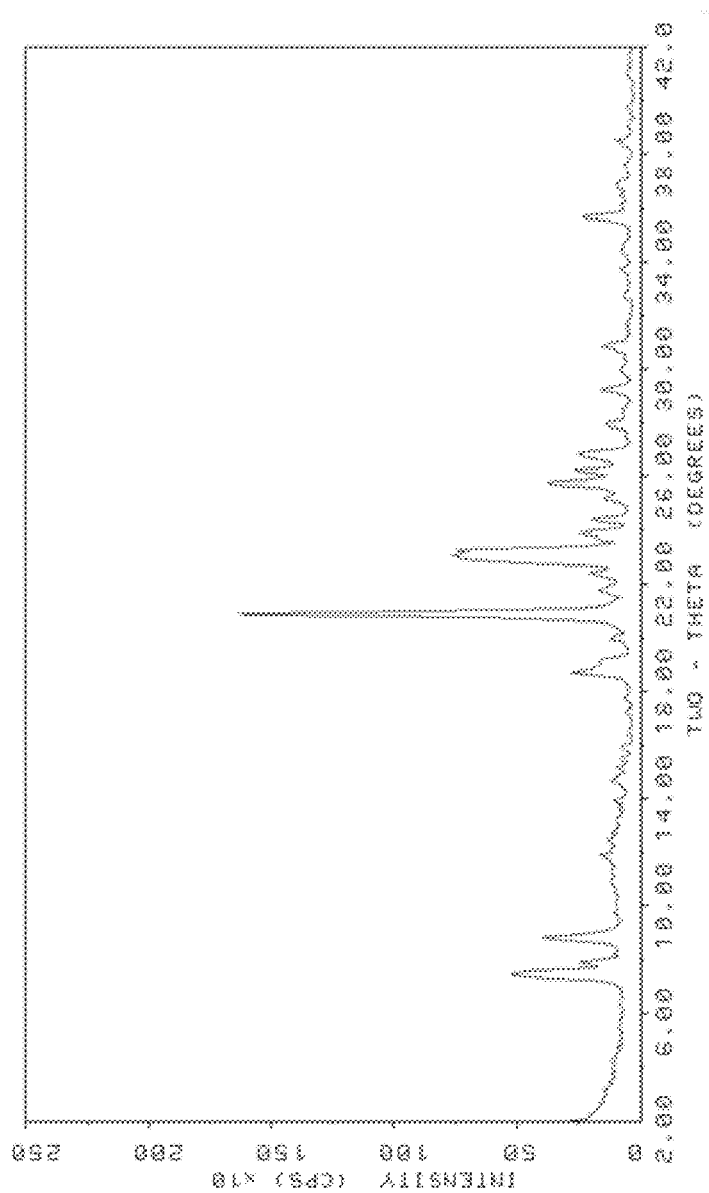
FIG. 1 shows a powder XRD pattern of impure ZSM-12 prepared according to Comparative Example 1.
Figure 2:
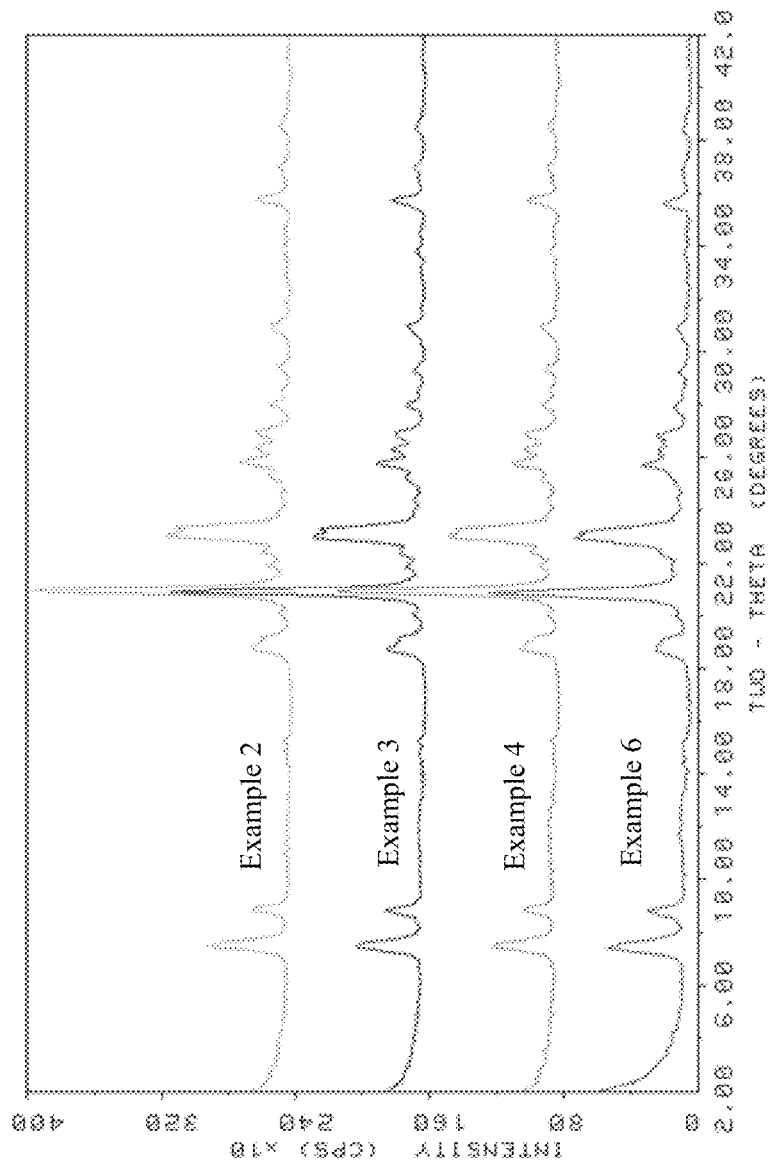
FIG. 2 shows a powder XRD pattern of pure aluminosilicate ZSM-12 prepared according to Examples 2-4 and 6 of the present invention.

The term "active source" means a reagent or precursor material capable of supplying at least one element in a form that can react and which may be incorporated into a zeolite structure. The terms "source" and "active source" may be used interchangeably herein.

The term "Periodic Table" refers to the version of IUPAC Periodic Table of the Elements dated Jun. 22, 2007, and the numbering scheme for the Periodic Table Groups is as described in Chemical and Engineering News, 63(5), 27 (1985).

The term "isomerization conditions" may be used herein to refer to one or more sets of physical and/or chemical parameters, such as a suitable temperature, pressure, feed rate, and catalyst composition, that allow or promote the isomerization of n-paraffins in a hydrocarbonaceous feed.

The term "isomerization selectivity" may be used herein to refer to the percentage of converted n-$C_{10}$+ alkanes in a hydrocarbon feed that are isomerized to isoparaffins in the product of a catalytic hydrocarbon conversion process.

Isoparaffin (i-) to normal (n-) paraffin ratios (i/n ratios) refer to weight ratios unless otherwise noted.

Where permitted, all publications, patents and patent applications cited in this application are herein incorporated by reference in their entirety, to the extent such disclosure is not inconsistent with the present invention.

Unless otherwise specified, the recitation of a genus of elements, materials or other components, from which an individual component or mixture of components can be selected, is intended to include all possible sub-generic combinations of the listed components and mixtures thereof. Also, the term "include" and its variants, are intended to be Non-limiting, such that recitation of items in a list is not to the exclusion of other like items that may also be useful in the materials, compositions, and methods of this invention.

Aluminosilicate and Borosilicate ZSM-12 Reaction Mixtures

In preparing aluminosilicate ZSM-12 (Al-ZSM-12), a 1,6-bis(2,3-dimethylimidazolium)hexane dication is used, either alone or in combination with a second nitrogen-containing structure directing agent (designated composition variable "A" herein below). The 1,6-bis(2,3-dimethylimidazolium) hexane useful for making Al-ZSM-12 is represented by the following structure (1):

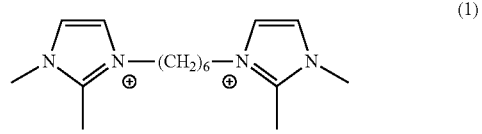

(1)

1,6-bis(2,3-dimethylimidazolium)hexane dication

In general, Al-ZSM-12 is prepared by:

(a) preparing a reaction mixture containing: (1) at least one source of silicon oxide; (2) at least one source of aluminum oxide; (3) at least one source of an element selected from Groups 1 and 2 of the Periodic Table; (4) hydroxide ions; (5) 1,6-bis(2,3-dimethylimidazolium)hexane cations; and (6) optionally, a second nitrogen-containing structure directing agent; and (b) maintaining the reaction mixture under conditions sufficient to form crystals of the Al-ZSM-12 molecular sieve.

The composition of the reaction mixture from which the aluminosilicate ZSM-12 molecular sieve is formed, in terms of molar ratios, is identified in Table 1 below:

TABLE 1

| Reactants | Broad | Preferred |
| --- | --- | --- |
| $SiO_2/Al_2O_3$ | 30-100 | 30-60 |
| $(Q + A)/SiO_2$ | 0.03-0.8 | 0.03-0.4 |
| Q/A | 0.05-∞ | 0.05-0.11 |
| $M/SiO_2$ | 0.05-1 | 0.15-0.3 |
| $OH^-/SiO_2$ | 0.1-1 | 0.2-0.5 |
| $H_2O/SiO_2$ | 20-80 | 30-70 | wherein:

(1) M is at least one element selected from Groups 1 and 2 of the Periodic Table;

(2) Q is cationic 1,6-bis(2,3-dimethylimidazolium)hexane, and Q>0; and (3) A is a second nitrogen-containing structure directing agent, and A≥0.

It should be noted that the Q/A molar ratio includes the case where there is no second nitrogen-containing structure directing agent (A) in the reaction mixture. In that case the reaction mixture only contains cationic 1,6-bis(2,3-dimethylimidazolium)hexane (Q) as the structure directing agent. In one subembodiment, the Q/A mole ratio is 0.05 to 0.3. In another subembodiment, the Q/A mole ratio is 0.05 to 0.2. In another subembodiment, the Q/A mole ratio is 0.05 to about 0.11.

According to one aspect of the instant invention, a small crystal form of aluminosilicate ZSM-12 can be prepared from a small crystal form of borosilicate ZSM-12 by post-synthetic replacement of the boron in the borosilicate ZSM-12 framework with aluminum. The small crystal form of the precursor borosilicate ZSM-12 may be prepared as described below. Then, replacement of boron in the borosilicate ZSM-12 with aluminum provides an alternative, yet facile, route to the synthesis of a low Si/Al ratio aluminosilicate ZSM-12 of small crystal size.

Replacement of boron in borosilicate ZSM-12 with aluminum may be readily achieved by suitable treatment of the borosilicate ZSM-12 with an aluminum salt, such as aluminum nitrate. In an embodiment, the proportion of boron in borosilicate ZSM-12 that may be replaced with aluminum according to the invention may be in the range of from about zero (0) to about 100%, typically from about 75% to about 100%, often from about 85% to about 100%. In a subembodiment, at least about 50% of the boron in the borosilicate framework is replaced with aluminum.

In preparing borosilicate ZSM-12 (B-ZSM-12), a 1,4-bis (trimethylammonium)butane dication or a 1,4-bis(N-methylpiperidinium)butane dication, represented by structures 2 and 3 below, respectively, is used as the structure directing agent.

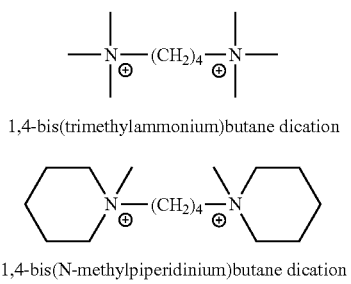

1,4-bis(trimethylammonium)butane dication (3)

1,4-bis(N-methylpiperidinium)butane dication

In general, borosilicate ZSM-12 is prepared by:

(a) preparing a reaction mixture containing: (1) at least one source of silicon oxide; (2) at least one source of boron oxide; (3) at least one source of an element selected from Groups 1 and 2 of the Periodic Table; (4) hydroxide ions; (5) cationic 1,4-bis(trimethylammonium)butane or cationic 1,4-bis(N-methylpiperidinium)butane as the structure directing agent; and (6) water; and (b) maintaining the reaction mixture under conditions sufficient to form crystals of the borosilicate ZSM-12.

The composition of the reaction mixture from which the borosilicate ZSM-12 molecular sieve is formed, in terms of molar ratios, is identified in Table 2 below:

TABLE 2

| Reactants | Broad | Preferred |
| --- | --- | --- |
| $SiO_2/B_2O_3$ | 10-100 | 20-60 |
| $X/SiO_2$ | 0.05-1 | 0.1-0.4 |
| $M/SiO_2$ | 0.1-1 | 0.2-0.4 |
| $OH^-/SiO_2$ | 0.1-0.6 | 0.2-0.4 |
| $H_2O/SiO_2$ | 20-100 | 30-60 | wherein M is at least one element selected from Groups 1 and 2 of the Periodic Table, and X is cationic 1,4-bis(trimethylammonium)butane or cationic 1,4-bis(N-methylpiperidinium)butane.

Sources of silicon oxide useful herein include fumed silica, precipitated silicates, silica hydrogel, silicic acid, colloidal silica, tetra-alkyl orthosilicates (e.g. tetraethyl orthosilicate), and silica hydroxides.

Sources of aluminum oxide useful herein include aluminates, alumina, and aluminum compounds such as $AlCl_3$, $Al_2SO_4$, $Al(OH)_3$, kaolin clays, and other zeolites.

Sources of boron oxide useful herein include borosilicate glasses, alkali borates, boric acid, borate esters, and certain zeolites. Non-limiting examples of a source of boron oxide include potassium tetraborate decahydrate and boron beta zeolite (B-beta zeolite).

A source of element M may be any M-containing compound which is not detrimental to the crystallization process. M-containing compounds may include oxides, hydroxides, nitrates, sulfates, halides, oxalates, citrates and acetates thereof. In one subembodiment, compositional variable M is sodium (Na) or potassium (K). In a subembodiment, an M-containing compound is an alkali metal halide, such as a bromide, iodide or potassium.

The molecular sieve reaction mixture can be supplied by more than one source. Also, two or more reaction components can be provided by one source. As an example, borosilicate molecular sieves may be synthesized from boron-containing beta molecular sieves, as taught in U.S. Pat. No. 5,972,204, issued Oct. 26, 1999 to Corma et al.

The optional second nitrogen-containing structure directing agent (A) used in the reaction mixture for synthesizing Al-ZSM-12 is an organic nitrogen containing compound, such as a linear or cyclic quaternary or diquaternary ammonium compound, suitable for synthesizing MTW-type materials. Structure directing agents suitable for synthesizing ZSM-12 are known in the art. (See, for example, Handbook of Molecular Sieves, Szostak, Van Nostrand Reinhold, 1992; U.S. Pat. No. 4,585,639, issued Apr. 29, 1986 to Szostak; and U.S. Pat. No. 4,482,531, issued Nov. 13, 1984 to Kuehl). Exemplary structure directing agents include: tetraalkylammonium cations such as methyltriethylammonium cations and tetraethylammonium cations; cationic dimethylpyrrolidinium; cationic dimethyl piperidinium; and cationic dimethylpyridinium.

The reaction mixture can be prepared either batch-wise or continuously. Crystal size, crystal morphology, and crystallization time of the aluminosilicate ZSM-12 of the present invention may vary with the nature of the reaction mixture and the crystallization conditions.

The structure directing agents (Q and A) are typically associated with anions which may be any anion that is not detrimental to the formation of the molecular sieve. Representative anions include chloride, bromide, iodide, hydroxide, acetate, sulfate, tetrafluoroborate, carboxylate, and the like.

Crystallization and Post-Synthesis Treatment

In practice, ZSM-12 is synthesized by: (a) preparing a reaction mixture as described hereinabove; and (b) maintaining the reaction mixture under crystallization conditions sufficient to form crystals of the molecular sieve. The reaction mixture is maintained at an elevated temperature until crystals of the molecular sieve are formed. The hydrothermal crystallization of the molecular sieve is usually conducted under pressure, and usually in an autoclave so that the reaction mixture is subject to autogenous pressure, typically at a temperature from about 140° C. to about 190° C., and usually from about 150° C. to about 170° C. for the aluminosilicate form, and from about 140° C. to about 200° C., and usually from about 150° C. to about 170° C. for the borosilicate form.

The reaction mixture may be subjected to mild stirring or agitation during the crystallization step. It will be understood by a person skilled in the art that the ZSM-12 molecular sieve described herein may contain one or more trace impurities, such as amorphous materials, phases having framework topologies which do not coincide with the zeolite, and/or other impurities (e.g., organic hydrocarbons).

During the hydrothermal crystallization step, crystals of ZSM-12 can be allowed to nucleate spontaneously from the reaction mixture. The use of crystals of the zeolite as seed material can be advantageous in decreasing the time necessary for complete crystallization to occur. In addition, seeding can lead to an increased purity of the product obtained by promoting the nucleation and/or formation of the zeolite over any undesired phases. When used as seeds, seed crystals are typically added in an amount from about 0.5% to about 5% of the weight of the source of silicon dioxide used in the reaction mixture.

Once the crystals have formed, the solid product may be separated from the reaction mixture by mechanical separation techniques such as filtration. The crystals are water washed and then dried to obtain "as-synthesized" crystals. The drying step can be performed at atmospheric pressure or under vacuum.

ZSM-12 may be used as-synthesized, but typically the zeolite will be thermally treated (calcined). The term "as-synthesized" refers to the ZSM-12 in its form after crystallization, prior to removal of the structure directing agent and/or element M. The organic material can be removed by thermal treatment (e.g., calcination), preferably in an oxidative atmosphere (e.g., air, or another gas with an oxygen partial pressure greater than 0 kPa), at a temperature (readily determinable by one skilled in the art) sufficient to remove the organic material from the zeolite. The organic material can also be removed by photolysis techniques, e.g., by exposing an SDA-containing zeolite product to light or electromagnetic radiation that has a wavelength shorter than visible light under conditions sufficient to selectively remove organic material from the zeolite, substantially as described in U.S. Pat. No. 6,960,327 to Navrotsky and Parikh.

Usually, it may also be desirable to remove alkali metal cations from the ZSM-12 by ion-exchange and to replace the alkali metal cations with hydrogen, ammonium, or a desired metal ion. The ZSM-12 can be combined with various metals, such as a metal selected from Groups 8-10 of the Periodic Table, including Pt, Pd, Ni, Rh, Ir, Ru, Os, or combinations thereof, by impregnation, or physical admixture, and the like, as well as ion-exchange.

Following ion-exchange, e.g., palladium exchange, the zeolite is typically washed with water and dried at temperatures ranging from 90° C. to about 120° C. After washing, the zeolite can be calcined in air, steam, or inert gas at a temperature ranging from about 315° C. to about 650° C. for periods ranging from about 1 to about 24 hours, or more, to produce a catalytically active product particularly useful in hydrocarbon isomerization and dewaxing processes.

Characterization of the Molecular Sieve

Aluminosilicate ZSM-12 prepared according to the teachings herein has a composition, as-synthesized and in the anhydrous state, as shown in Table 3 in terms of mole ratios:

TABLE 3

| | |
|---|---|
| $SiO_2/Al_2O_3$ | 30-100 |
| $(Q + A)/SiO_2$ | 0.015-0.06 |
| $M/SiO_2$ | 0-0.1 | wherein M, Q and A are as described hereinabove.

Aluminosilicate ZSM-12 prepared according to the present invention has a $SiO_2/Al_2O_3$ mole ratio generally from about 30 to about 100, and in one subembodiment from about 30 to about 80, and in another subembodiment from about 30 to about 60. Aluminosilicate ZSM-12 of the present invention typically crystallizes as aggregates of intergrown crystals, wherein each aggregate contains a plurality of elongated crystallites. Each individual crystallite may be needle-like with a width in the range from about 15 to about 25 nm and a length in the range from about 60 to about 80 nm, with average dimensions of the crystallites of about 20 nm by about 60 nm.

ZSM-12 products synthesized by the methods described herein are characterized by their powder X-ray diffraction (XRD) pattern. Minor variations in the diffraction pattern can result from variations in the mole ratios of the framework species of the particular borosilicate ZSM-12 sample due to changes in lattice constants. In addition, sufficiently small crystals will affect the shape and intensity of peaks, leading to significant peak broadening. Minor variations in the diffraction pattern can also result from variations in the structure of the organic template used in the zeolites preparation. Calcination can also cause minor shifts in the powder XRD pattern. Notwithstanding these minor perturbations, the basic crystal lattice structure remains unchanged.

The XRD pattern lines of Table 4 are representative of as-synthesized aluminosilicate ZSM-12 made in accordance with the teachings presented herein.

TABLE 4

Characteristic powder XRD peaks for as-synthesized aluminosilicate ZSM-12

| 2 Theta[a] | d-spacing (Angstroms) | Relative Intensity[b] |
|---|---|---|
| 7.48 | 11.82 | M |
| 8.80 | 10.04 | W |
| 18.74 | 4.73 | W |
| 19.10 | 4.64 | W |
| 19.93 | 4.45 | W |
| 20.85 | 4.26 | VS |
| 21.77 | 4.08 | W |
| 22.36 | 3.97 | W |
| 22.98 | 3.87 | S |
| 23.24 | 3.82 | W |
| 25.32 | 3.52 | W |
| 25.72 | 3.46 | W |
| 26.24 | 3.39 | W |
| 26.80 | 3.32 | W |
| 27.89 | 3.20 | W |
| 29.21 | 3.05 | W |
| 30.81 | 2.90 | W |
| 35.61 | 2.52 | W |

[a] ±0.25
[b] Based on a relative intensity scale in which the strongest line in the X-ray pattern is assigned a value of 100: W (weak) is less than 20; M (medium) is between 20 and 40; S (strong) is between 40 and 80; VS (very strong) is greater than 80.

The XRD pattern lines of Table 5 are representative of calcined aluminosilicate ZSM-12 made in accordance with the teachings presented herein.

TABLE 5

Characteristic powder XRD peaks for calcined aluminosilicate ZSM-12

| 2 Theta[a] | d-spacing (Angstroms) | Relative Intensity[b] |
|---|---|---|
| 7.51 | 11.76 | M |
| 8.86 | 9.98 | W |
| 14.81 | 5.98 | W |
| 15.28 | 5.80 | W |
| 18.75 | 4.73 | W |
| 19.11 | 4.64 | W |
| 20.03 | 4.43 | W |
| 20.91 | 4.25 | VS |
| 21.98 | 4.04 | W |
| 22.42 | 3.96 | W |
| 22.98 | 3.88 | W |
| 23.24 | 3.82 | M |
| 25.21 | 3.53 | W |
| 25.78 | 3.45 | W |
| 26.33 | 3.38 | W |
| 26.86 | 3.32 | W |
| 27.99 | 3.19 | W |
| 29.33 | 3.04 | W |
| 30.88 | 2.89 | W |
| 35.71 | 2.51 | W |
| 36.97 | 2.43 | W |
| 38.57 | 2.33 | W |

[a] ±0.25
[b] Based on a relative intensity scale in which the strongest line in the X-ray pattern is assigned a value of 100: W (weak) is less than 20; M (medium) is between 20 and 40; S (strong) is between 40 and 80; VS (very strong) is greater than 80.

Borosilicate ZSM-12 prepared according to the present invention has a composition, as-synthesized and in the anhydrous state, as shown in Table 6, in terms of mole ratios, wherein X and M are as described hereinabove:

TABLE 6

| | |
|---|---|
| $SiO_2/B_2O_3$ | 40-100 |
| $X/SiO_2$ | 0.02-0.06 |
| $M/SiO_2$ | 0-0.1 |

Borosilicate ZSM-12 of the present invention typically crystallizes as ellipsoidal aggregates of intergrown crystals, wherein the aggregates have a length of about 1 μm and a width in the range from about 0.3 μm to about 0.5 μm.

The XRD pattern lines of Table 7 are representative of as-synthesized borosilicate ZSM-12 made in accordance with the teachings presented herein.

TABLE 7

Characteristic powder XRD peaks for as-synthesized B-ZSM-12

| 2 Theta[a] | d-spacing (Angstroms) | Relative Intensity[b] |
|---|---|---|
| 7.61 | 11.61 | M |
| 8.86 | 9.97 | W |
| 19.12 | 4.64 | W |
| 20.31 | 4.37 | W |
| 21.17 | 4.19 | VS |
| 22.10 | 4.02 | W |
| 22.75 | 3.90 | W |
| 23.30 | 3.81 | S |
| 25.51 | 3.49 | W |
| 26.10 | 3.41 | W |
| 26.62 | 3.35 | W |
| 26.98 | 3.30 | W |
| 28.29 | 3.15 | W |
| 29.61 | 3.02 | W |

[a] ±0.25
[b] Based on a relative intensity scale in which the strongest line in the X-ray pattern is assigned a value of 100: W (weak) is less than 20; M (medium) is between 20 and 40; S (strong) is between 40 and 80; VS (very strong) is greater than 80.

The powder XRD patterns and data presented herein were collected by standard techniques. The radiation was CuK-α radiation. The peak heights and the positions, as a function of 2θ where θ is the Bragg angle, were read from the relative absolute intensities of the peaks, and d, the interplanar spacing in Angstroms corresponding to the recorded lines, can be calculated.

Applications for Aluminosilicate ZSM-12

Catalyst Compositions Comprising Al-ZSM-12

Catalyst compositions comprising aluminosilicate ZSM-12 of the present invention may have a composition, in terms of weight percent, as shown in Table 8:

TABLE 8

| Component | Broad | Secondary |
|---|---|---|
| aluminosilicate ZSM-12 | 1-99% | 15-50% |
| binder | 1-99% | 50-85% |
| Group 8-10 metals(s) and other elements | 0-5% | 0.5-1.5% |

For commercial applications as a catalyst, the aluminosilicate ZSM-12 may be formed into a suitable size and shape. This forming can be done by techniques such as pelletizing, extruding, and combinations thereof. In the case of forming by extrusion, extruded materials can be cylinders, trilobes, fluted, or have other shapes, which may be axially symmetrical, and that promote diffusion and access of feed materials to interior surfaces of the aluminosilicate ZSM-12 extrusion product.

In preparing catalysts for use in processes of the present invention, the aluminosilicate ZSM-12 crystals can be composited with binders resistant to the temperatures and other conditions employed in hydrocarbon conversion processes. Binders may also be added to improve the crush strength of the catalyst.

The binder material may comprise one or more refractory oxides, which may be crystalline or amorphous, or can be in the form of gelatinous precipitates, colloids, sols, or gels. Silica in the form of a silica sol is a preferred binder. A preferred silica sol has about 30 wt % silica and a particle size of about 7-9 nm in diameter, which provides catalysts having good attrition resistance and excellent crush strengths.

Forming pellets or extrudates from molecular sieves, including the small crystal forms of aluminosilicate ZSM-12 useful in this invention, generally involves using extrusion aids and viscosity modifiers in addition to binders. These additives are typically organic compounds such as cellulose based materials, for example, METHOCEL cellulose ether (Dow Chemical Co.), ethylene glycol, and stearic acid. Such compounds are known in the art. It is important that these additives do not leave a detrimental residue, i.e., one with undesirable reactivity or one that can block pores of the zeolite, after pelletizing.

Methods for preparing catalyst compositions are well known to those skilled in the art and include such conventional techniques as spray drying, pelletizing, extrusion, various sphere-making techniques, and the like.

The relative proportions of the aluminosilicate ZSM-12 and binder can vary widely. Generally, the aluminosilicate ZSM-12 content ranges from about 1 to about 99 weight percent (wt %) of the dry composite, usually in the range of from about 5 to about 95 wt % of the dry composite, and more typically from about 15 to about 50 wt % of the dry composite.

The catalyst can optionally contain one or more metals selected from Groups 8-10 of the Periodic Table. In one subembodiment, the catalyst contains a metal selected from the group consisting of Pt, Pd, Ni, Rh, Ir, Ru, Os, and mixtures thereof. In another subembodiment, the catalyst contains palladium (Pd) or platinum (Pt). For each embodiment described herein, the Group 8-10 metal content of the catalyst may be generally in the range of from 0 to about 10 wt %, typically from about 0.05 to about 5 wt %, usually from about 0.1 to about 3 wt %, and often from about 0.3 to about 1.5 wt %. In an embodiment, the aluminosilicate ZSM-12 can be palladium exchanged.

Additionally, other elements may be used in combination with the metal selected from Groups 8-10 of the Periodic Table. Examples of such "other elements" include Sn, Re, and W. Examples of combinations of elements that may be used in catalyst materials of the present invention include, without limitation, Pt/Sn, Pt/Pd, Pt/Ni, and Pt/Re. These metals or other elements can be readily introduced into the aluminosilicate ZSM-12 composite using one or more of various conventional techniques, including ion-exchange, pore-fill impregnation, or incipient wetness impregnation. Reference to the catalytically active metal or metals is intended to encompass such metal or metals in the elemental state or in some form such as an oxide, sulfide, halide, carboxylate, and the like.

Selective Isomerization of n-paraffins to Isoparaffins

Aluminosilicate or borosilicate ZSM-12, prepared according to the novel methods described herein may be useful in catalytic hydrocarbon conversion processes involving n-paraffin selective isomerization. In contrast, "cracking" refers to processes or reactions that decrease the molecular weight of hydrocarbons by breaking them into smaller components.

Catalyst compositions comprising aluminosilicate ZSM-12 of the invention show a high propensity for isomerization of n-paraffins with high conversion at relatively low temperatures (e.g., 260° C. to 280° C.), and hence a low propensity for cracking. Moreover, catalyst compositions of the present invention are highly selective for the production of dimethyl isoparaffins over monomethyl isoparaffins (see, e.g., Table 9).

According to the present invention, a process for converting hydrocarbons includes contacting a hydrocarbonaceous feed under isomerization conditions with aluminosilicate ZSM-12 synthesized as described herein, and having a $SiO_2/Al_2O_3$ mole ratio from about 30 to about 100, and in one subembodiment from about 30 to about 80, and in another subembodiment, from about 30 to about 60.

Catalyst compositions of the instant invention may be used to dewax a variety of feedstocks ranging from relatively light distillate fractions, such as kerosene and jet fuel, up to high boiling stocks such as whole crude petroleum, reduced crudes, vacuum tower residua, cycle oils, synthetic crudes (e.g., shale oils, tars and oil, etc.), gas oils, vacuum gas oils, foots oils, Fischer-Tropsch derived waxes, and other heavy oils. Straight chain n-paraffins either alone or with only slightly branched chain paraffins having 16 or more carbon atoms are sometimes referred to herein as waxes.

The feedstock will often be a $C_{10+}$ feedstock generally boiling above about 177° C. Processes of the present invention may be particularly useful with waxy distillate stocks such as middle distillate stocks including gas oils, kerosenes, and jet fuels, lubricating oil stocks, heating oils and other distillate fractions whose pour point and viscosity need to be maintained within certain specification limits. Lubricating oil stocks will generally boil above 230° C., more usually above 315° C. Hydroprocessed stocks are a convenient source of stocks of this kind and also of other distillate fractions since they normally contain significant amounts of waxy n-paraffins.

Feedstocks for processes of the present invention may contain paraffins, olefins, naphthenes, aromatic and heterocyclic compounds and may have a substantial proportion of higher molecular weight n-paraffins and slightly branched paraffins which contribute to the waxy nature of the feedstock. During the processing, the n-paraffins and the slightly branched paraffins may undergo a relatively low degree of cracking at high conversion.

Examples of some typical feedstocks which may be used in processes of the instant invention include hydrotreated or hydrocracked gas oils, hydrotreated lube oil raffinates, brightstocks, lubricating oil stocks, synthetic oils, foots oils. Fischer-Tropsch synthesis oils, high pour point polyolefins, normal alphaolefin waxes, slack waxes, de-oiled waxes and microcrystalline waxes.

In an embodiment, the present invention provides processes for hydroconverting a hydrocarbonaceous feed which comprises $C_{10+}$ n-paraffins. Such processes may comprise contacting the feed in the presence of hydrogen and under isomerization conditions with a catalyst composition comprising aluminosilicate ZSM-12 to provide an isoparaffin product with an isomerization selectivity of at least about 80% at greater than about 90% conversion of the feed. The aluminosilicate ZSM-12 may be prepared, and may have characteristics and features, as described herein.

The conditions for isomerization dewaxing processes of the present invention generally include a temperature typically within a range from about 240° C. to about 320° C., usually from about 255° C. to about 290° C., often from about 260° C. to about 280° C.; and a pressure from about 15 to about 5000 psig, typically from about 50 to about 3000 psig, and often from about 100 to about 2500 psig. The contacting of the feed with the catalyst is generally carried out in the presence of hydrogen. The hydrogen to hydrocarbon ratio is generally within a range from about 2000 to about 10,000 standard cubic feet $H_2$ per barrel of hydrocarbon, and typically from about 2500 to about 5000 standard cubic feet $H_2$ per barrel of hydrocarbon. The liquid hourly space velocity (LHSV) during contacting is generally from about 0.1 to about 20, more usually from about 0.1 to about 5, and often from about 0.5 to about 5.

According to an aspect of the invention, n-hexadecane may be used as a model compound, to represent a "heavier" n-alkane feed, for the identification of catalysts that selectively isomerize heavier (e.g., $C_{10+}$) normal paraffins providing relatively high levels of isoparaffin products, with much lower levels of cracking. In a subembodiment, n-hexadecane may be used to identify n-paraffin isomerization selective catalysts that isomerize n-$C_{10+}$ alkanes to an isoparaffin product comprising predominantly dimethyl isoalkanes.

Isomerization dewaxing processes of the invention provide an isoparaffin conversion product comprising a mixture of monomethyl- and dimethyl isoalkanes. For a hydrocarbon feed comprising n-hexadecane, processes of the present invention provide an isoparaffin product which may include dimethyl $C_{14}$ alkanes together with monomethyl $C_{15}$ alkanes, wherein the dimethyl isoalkanes may predominate over the monomethyl isoalkanes. Stated alternatively, dimethyl isoalkanes may comprise more than 50% of the isoalkanes in the product. In an embodiment, at a temperature from about 260° C. to about 280° C. the ratio of dimethyl isoparaffins to monomethyl isoparaffins in the product is at least about 2. In some embodiments, the dimethyl isoalkanes may generally comprise more than about 66% of the isoalkanes in the product, typically more than about 70%, often at least about 75%, and in one embodiment about 80%, of the isoalkanes in the product.

In one embodiment of the present invention, at a temperature from about 260° C. to about 280° C. a selective isomerization catalyst comprising aluminosilicate ZSM-12 converts at least about 96% of n-paraffins in the feed to provide a product comprising isoparaffins with an isomerization selectivity of at least about 85% (≤15% cracking). In a subembodiment, the feed may be contacted with the catalyst under isomerization conditions comprising a temperature in the range of about 265° C. to about 270° C. to provide at least about 95% conversion of n-hexadecane with an isomerization selectivity of at least about 88% (≤12% cracking).

In a subembodiment, a catalyst composition of the present invention under isomerization conditions at a temperature of about 260-280° C. provides at least about 96% conversion of n-hexadecane in the feed with an iso-$C_{16}$ yield of at least about 75%. In another subembodiment, for example, the catalyst composition may provide an iso-$C_{16}$ yield in the range from about 84% to about 88%.

In another embodiment, at a temperature of about 280° C. an isomerization selective catalyst of the present invention provides a $C_{10}$ alkane product from an n-hexadecane feed, wherein the $C_{10}$ alkane product has an iso/normal weight ratio of at least about 45 (under the conditions defined in Example 13).

The hydrocarbonaceous feed can be contacted with the catalyst in a fixed bed system, a moving bed system, a fluidized system, a batch system, or combinations thereof. Reactors similar to those employed in hydrotreating and hydrocracking are suitable. Either a fixed bed system or a moving bed system is preferred. In a fixed bed system, the preheated feed is passed into at least one reactor that contains a fixed bed of the catalyst prepared from the aluminosilicate ZSM-12 zeolite of the invention. The flow of the feed can be upward, downward or radial. Interstage cooling can be performed, for example, by injection of cool hydrogen between reactor beds. The reactors can be equipped with instrumentation to monitor and control temperatures, pressures, and flow rates that are typically used in hydrocrackers. Multiple beds may also be used in conjunction with compositions and processes of the invention, wherein two or more beds may each contain a different catalytic composition, at least one of which may comprise aluminosilicate ZSM-12 of the present invention.

EXAMPLES

The following examples demonstrate but do not limit the present invention.

Comparative Example 1

Synthesis of ZSM-12 Zeolite Using Methyltriethylammonium Chloride

This is a comparative example showing the preparation of impure ZSM-12 when using methyltriethylammonium cation as sole organic component in the reaction mixture, i.e., in the absence of a diquaternary dication structure directing agent.

105.6 g of sodium silicate solution (Fisher brand, 28 wt % $SiO_2$, 8.9 wt % $Na_2O$) was mixed with 104.4 g of deionized water inside a 600-mL Teflon liner. Next 40 g of a 75% methyltriethylammonium chloride solution (Sachem) was dissolved in 120.5 g of deionized water and mixed with the silicate solution. Then 4.02 g of aluminum nitrate nonahydrate was dissolved in 227.1 g of deionized water. The aluminum nitrate solution was then added to the silicate solution with continuous stirring to form a uniform suspension. Next 6.4 g of sulfuric acid (98%) was added to the suspension and mixed to form a uniform gel. The gel was mixed for an hour. The liner was then sealed within a Parr Steel autoclave reactor. The autoclave was heated under static conditions to 155° C. over a 4-hr period and then allowed to remain at 155° C. for 80 hours. The solid products were recovered from the cooled reactor by vacuum filtration and washed with copious quantities of water. The solids were then allowed to dry in an oven at 95° C. for over 12 hours. The powder XRD pattern (FIG. 1) indicated the product was ZSM-12 with minor amounts of ZSM-5 as an impurity.

Direct Synthesis of Small Crystal Al-ZSM-12

Examples 2-6

Example 2

105.6 g of sodium silicate solution (Fisher brand, 28 wt % $SiO_2$, 8.9 wt % $Na_2O$) was mixed with 104.4 g of deionized water inside a 600-mL Teflon liner. Next, in a second step, 32 g of a 75% methyltriethylammonium chloride solution (Sachem) and 11.02 g of 1,6-bis(2,3-dimethylimidazolium)hexane dibromide salt were dissolved in 122.5 g of deionized water, and this solution was mixed with the silicate solution. Then 4.02 g of aluminum nitrate nonahydrate was dissolved in 227.1 g of deionized water. The aluminum nitrate solution was added to the silicate solution with continuous stirring to form a uniform suspension. Next 6.4 g of sulfuric acid (98%) was added to the suspension and mixed to form a uniform gel. The gel was mixed for an hour. The liner was then sealed within a Parr Steel autoclave. The autoclave was heated under static conditions to 155° C. over a 4-hr period and then allowed to remain at 155° C. for 80 hours. The solid products were recovered from the cooled reactor by vacuum filtration and washed with copious quantities of water. The solids were then allowed to dry in an oven at 95° C. for over 12 hours. The powder X-ray diffraction pattern indicated the product was pure ZSM-12. Peak broadening in the XRD pattern is entirely consistent with the small crystallite size as noted hereinabove.

Example 3

Example 2 was repeated except 36.29 g of 75% methyltriethylammonium chloride solution, 5.51 g of 1,6-bis(2,3-dimethylimidazolium)hexane dibromide salt, and 121.52 g of deionized water were used in the second step. The powder XRD pattern indicated the product was pure ZSM-12.

Example 4

Example 2 was repeated using 38.04 g of 75% methyltriethylammonium chloride solution, 2.75 g of 1,6-bis(2,3-dimethylimidazolium)hexane dibromide salt, and 121 g of deionized water in the second step. The powder XRD pattern indicated the product was pure ZSM-12.

Comparative Example 5

Example 2 was repeated except 7.02 g of aluminum nitrate nonahydrate was used (instead of 4.02 g of aluminum nitrate nonahydrate). The autoclave was heated under static conditions to 155° C. over a 4-hr period and then allowed to remain at 155° C. for 5 days. The powder X-ray diffraction pattern indicated the product was ZSM-12 with a trace impurity of mordenite.

Example 6

Comparative Example 5 was repeated except instead of heating under static conditions, the gel was mixed with an overhead stirrer at 75 rpm. The powder XRD pattern indicated the product was pure ZSM-12. The Si/Al ratio of this preparation of aluminosilicate ZSM-12 was determined to be 22.

Synthesis of Small Crystal Borosilicate ZSM-12

Examples 7-10

Example 7

3.49 g of an aqueous solution of 1,4-bis(trimethylammonium)butane dihydroxide ([OH]=0.86 mmol/g), 0.37 g of potassium iodide, and 7.71 g of deionized water were mixed together. Then 0.035 g of potassium tetraborate decahydrate (KTB) was dissolved in the solution, and 0.90 g of CAB-O-SIL M-5 (Cabot Corporation) was added and mixed to form a uniform suspension. The mixture was placed in a Teflon cup, capped, and placed within a sealed 23-ml stainless steel Parr autoclave. The autoclave was placed in a spit within an oven at 160° C. and mixed at 43 rpm for 7 days. The reactor was removed from the oven, allowed to cool, and the solids were collected by filtration and washing with deionized water. The solids were then allowed to dry within an oven at 95° C. The Si/B ratio of the product, measured by Inductively Coupled Plasma—Optical Emission Spectroscopy (ICP-OES), was 31.8.

Examples 8 and 9

Two preparations of borosilicate ZSM-12 were performed as in Example 7, except 0.07 g of KTB was used in one (Example 8) and 0.10 g of KTB was used in the other (Example 9). The Si/B ratios of the products from Example 8 and 9 were 34.7 and 28.0, respectively.

Figure 3:
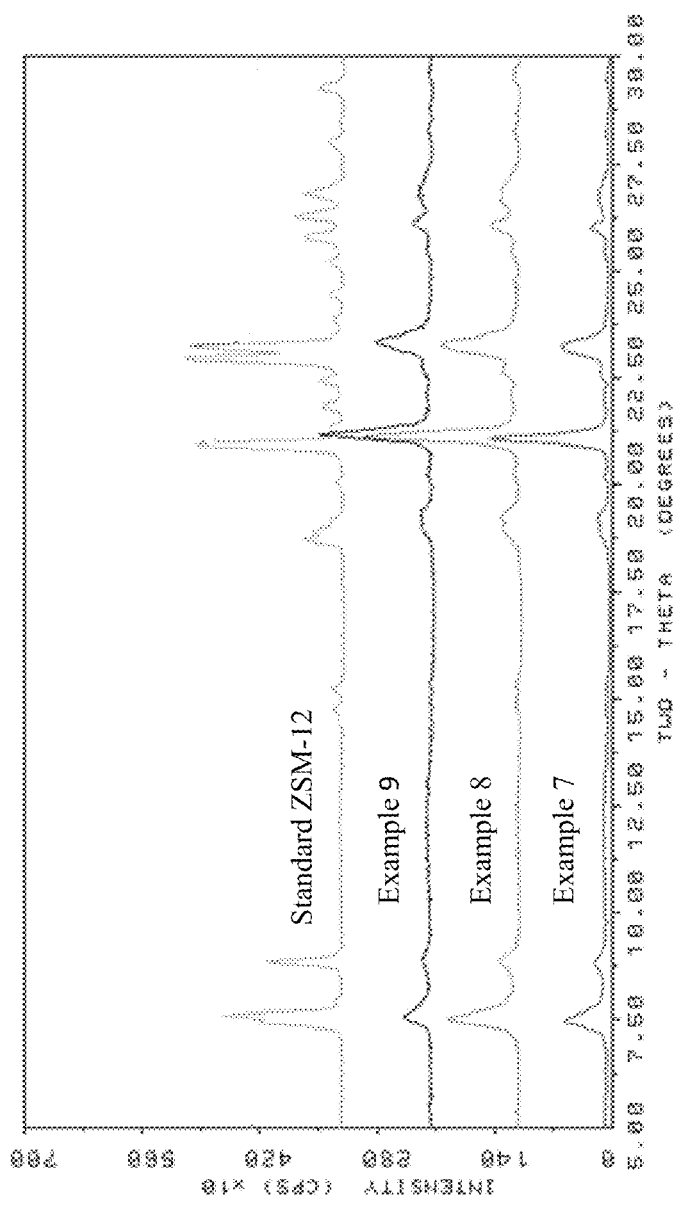
FIG. 3 shows powder XRD patterns of borosilicate ZSM-12 prepared according to Examples 7-9 of the present invention, in comparison with the pattern for a conventional (standard) sample of aluminosilicate ZSM-12.
Figure 4:
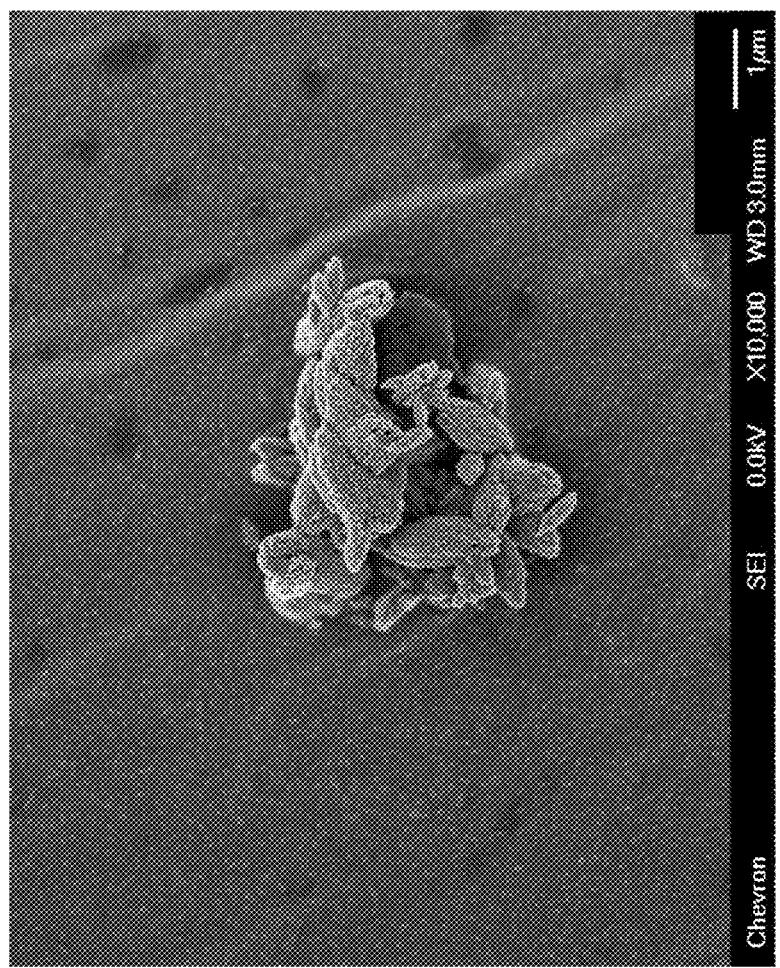
FIGS. 4 and 5 show a scanning electron micrograph of the borosilicate ZSM-12 prepared according to Example 8 of the present invention.
Figure 5:
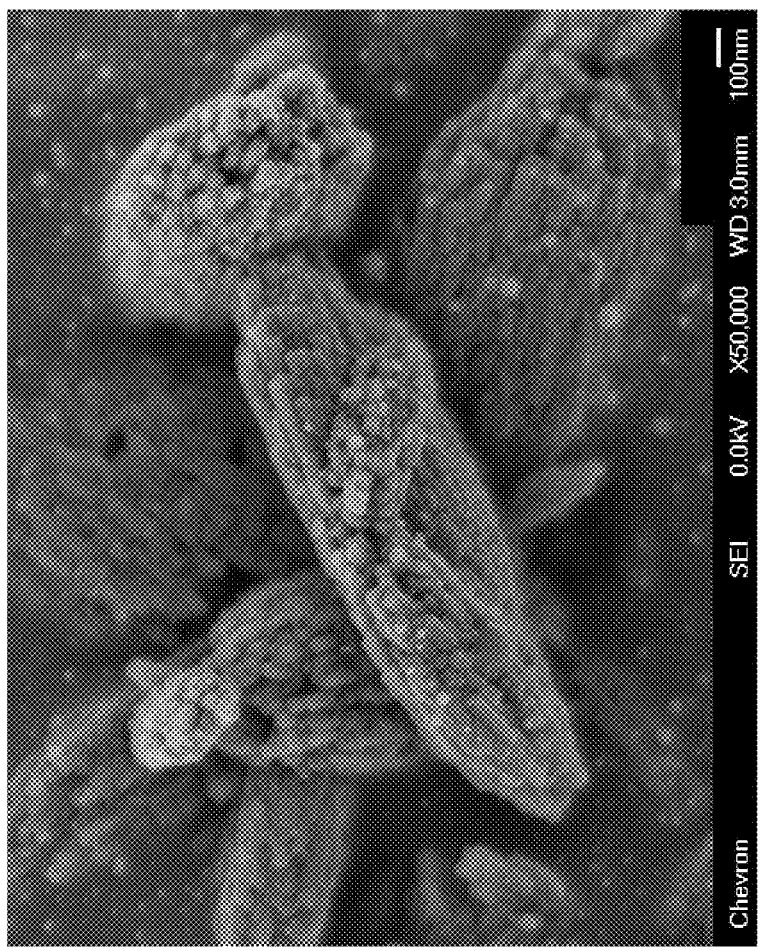

FIG. 3 shows the powder XRD patterns of the products from Example 7, Example 8 and Example 9, compared with that of a standard (conventional) ZSM-12. The broader peaks of the patterns for the B-ZSM-12 products of Examples 7-9 are consistent with the smaller crystal sizes of each preparation. Interestingly, for the three samples in this series, it appears that the gel with the highest boron concentration yields a zeolite product with the broadest diffraction peaks. FIGS. 4 and 5 show scanning electron micrographs (SEM) of the product of Example 8. The crystalline aggregates were ellipsoids about 1 μm long and 0.3-0.5 μm in width. The individual crystallites within each aggregate were fine needles with a width in the range from about 30 nm to about 40 nm.

Example 10

5.94 g of an aqueous solution of 1,4-bis(N-methylpiperidinium)butane dihydroxide ([OH]=0.51 mmol/g), 0.37 g of potassium iodide, and 4.86 g of deionized water were mixed together. Then 0.035 g of potassium tetraborate decahydrate (KTB) was dissolved in the solution, and 0.90 g of CAB-O-SIL M-5 was added and mixed to form a uniform suspension. The gel was then heated as described in Example 7. The product of this preparation was identified by powder XRD analysis as B-ZSM-12.

Example 11

Indirect Synthesis of Small Crystal Al-ZSM-12 from Small Crystal B-ZSM-12

The small crystal B-ZSM-12 product from Example 8 was calcined to a temperature of 595° C. to remove the organic from the zeolite. The calcination was performed in a muffle furnace by heating in 4% oxygen/nitrogen at 1° C./min to 595° C. and maintaining the temperature at 595° C. for 6 hours. 0.71 g of calcined zeolite was then added to 15 mL of a 1M solution of aluminum nitrate in a Teflon liner. The Teflon liner was capped and sealed within a stainless steel Parr autoclave. The autoclave was heated at 160° C. overnight. After cooling, the solids were removed by filtration and washed with ~500 mL of deionized water to provide small crystal aluminosilicate ZSM-12.

Figure 6:
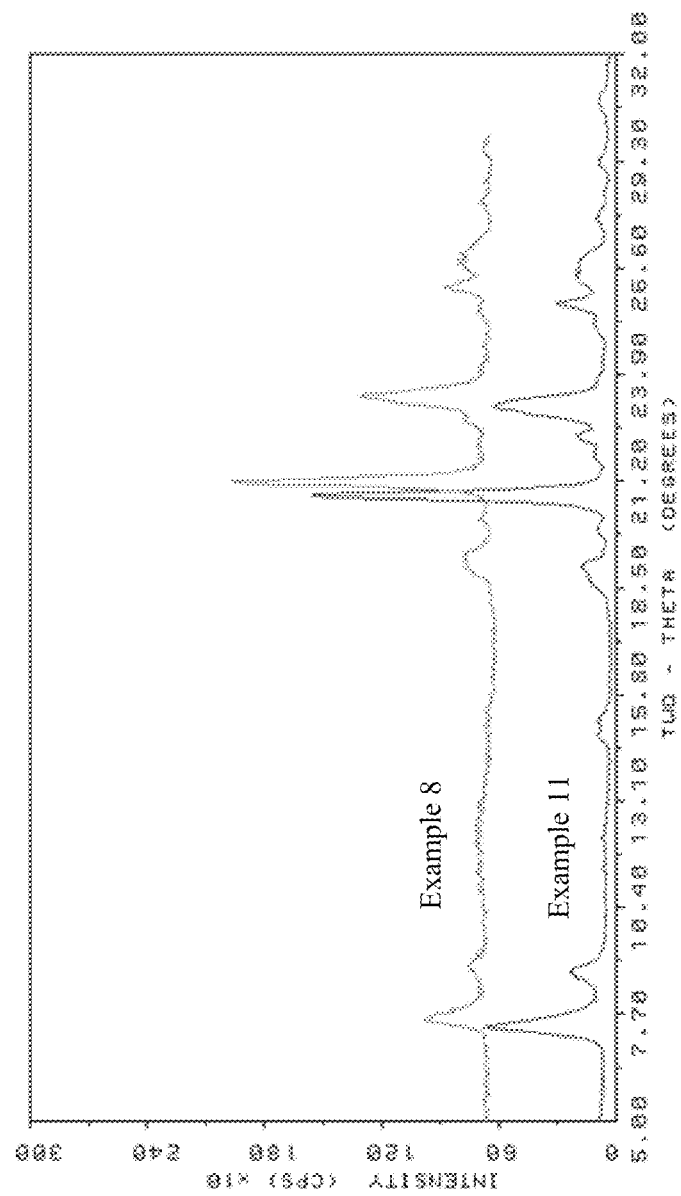
FIG. 6 shows a powder XRD pattern of the aluminosilicate ZSM-12 prepared according to Example 11 of the present invention, in comparison with the pattern for borosilicate ZSM-12.

FIG. 6 compares the powder XRD pattern for the product of this preparation (Example 11) with that of the original (precursor) material of Example 8. The shifts in the diffraction peaks to lower angles are consistent with expansion of the zeolite lattice when aluminum is inserted into the framework. The Al-ZSM-12 product was then exchanged to the ammonium form using the following procedure. 0.59 g of zeolite was added to a solution of 0.59 g of ammonium nitrate in 5.8 g of deionized water. The exchange was allowed to proceed overnight at 95° C. The zeolite was then recovered by filtration and a second ammonium exchange was carried out.

Example 12

Palladium Exchange of Indirectly Synthesized Aluminosilicate ZSM-12

After the ammonium-exchange of small crystal Al-ZSM-12 (Example 11), the zeolite was palladium-exchanged as follows. 0.59 g of the Al-ZSM-12 was added to a solution prepared by mixing 2.56 g of 0.156 N ammonium hydroxide, 4.41 g of deionized water, and 0.59 g of a solution of $Pd(NH_3)_4(NO_3)_2$. The palladium solution was formed by dissolving 0.72 g of $Pd(NH_3)_4(NO_3)_2$ in 42.01 g of deionized water and 6.00 g of 0.148 M ammonium hydroxide solution. The pH of the resultant slurry was adjusted to 10.0 with drops of ammonium hydroxide. The exchange was allowed to proceed for 2 days. The solids were then recovered by filtration and allowed to dry. The palladium exchanged zeolite was then calcined in a muffle furnace by heating at 1° C./min to 482° C. and maintaining the temperature at 482° C. for 3 hours. The catalytic activity of the calcined palladium exchanged zeolite was tested for n-hexadecane conversion (see, e.g., Example 13).

Example 13

Conversion of n-hexadecane Over Pd-exchanged Al-ZSM-12

Palladium-exchanged aluminosilicate ZSM-12 (Pd/Al-ZSM-12) prepared according to Example 13 was used for the selective isomerization of n-hexadecane under the conditions of temperature, pressure, weight hourly space velocity (WHSV), and hydrogen inlet (MSCFB) as given in Table 9, infra.

Products were analyzed by on-line capillary gas chromatography (GC). Raw data from the GC was collected by an automated data collection/processing system and hydrocarbon conversions were calculated from the raw data. Yields were expressed as weight percent product. For the purpose of this example, isomerization selectivity is defined as the percentage of $n-C_{16}$ in the feed that is isomerized to isoparaffins in the product.

The data are summarized in Table 9. For this sample, a temperature of about 282° C. (540° F.) was necessary for 94% conversion. At this temperature, isomerization selectivity was 82.6 (17.4% cracking). This selectivity was somewhat lower than that observed in Example 13, but again there was a strong preference for the production of dimethyl-$C_{14}$ (>64%), as compared with monomethyl $C_{15}$, in the isoparaffin distribution. These data demonstrate that borosilicate ZSM-12 (precursor) of the present invention can be successfully transformed, e.g., according to the procedure of Example 12, into an aluminosilicate acid catalyst for use in isomerization selective hydroconversion processes.

TABLE 9

Summary of $n-C_{16}$ conversion and selectivity at different temperatures for small-crystal Al-ZSM-12

| | Measured Data | | | | |
|---|---|---|---|---|---|
| Temperature (° C.) | 288 | 285 | 282 | 283 | 284 |
| WHSV | 1.55 | 1.55 | 1.55 | 1.55 | 1.55 |
| Pressure (psig) | 1200 | 1200 | 1200 | 1200 | 1200 |
| H2 Inlet, MSCFB | 53.9 | 53.9 | 53.9 | 53.9 | 53.9 |
| $nC_{16}$ Conv. | 98.3 | 97.4 | 94.4 | 95.7 | 96.4 |
| $nC_{16}$ Tot Rate | 6.34 | 5.62 | 4.47 | 4.86 | 5.13 |
| $nC_{16}$ Crack Conv. | 28.4 | 23.7 | 16.4 | 18.5 | 20.2 |
| $nC_{16}$ Crack Rate | 0.52 | 0.42 | 0.28 | 0.32 | 0.35 |
| Selectivity % | | | | | |
| Isomerization | 71.1 | 75.7 | 82.6 | 80.7 | 79 |
| Total Cracking | 28.9 | 24.4 | 17.4 | 19.3 | 21 |
| $C_{4-}$ Cracking | 3.2 | 2.7 | 1.8 | 2 | 2.2 |
| $C_{5+}$ Cracking | 25.8 | 21.8 | 15.6 | 17.4 | 18.9 |
| $C_{5+}/C_{4-}$ | 8.1 | 8.3 | 8.6 | 8.7 | 8.7 |
| $C_{5+}C6/C_{5+}$ % | 23.85 | 23.51 | 22.57 | 22.57 | 22.92 |
| C6 DMB/MP | 0.12 | 0.12 | 0.1 | 0.1 | 0.12 |

TABLE 9-continued

Summary of n-$C_{16}$ conversion and selectivity at different temperatures for small-crystal Al-ZSM-12

| | Measured Data | | | | |
|---|---|---|---|---|---|
| i/n Ratios | | | | | |
| $C_4$ i/n | 3.12 | 3.08 | 3.01 | 3.04 | 3.09 |
| $C_5$ i/n | 3.57 | 3.58 | 3.52 | 3.59 | 3.62 |
| $C_6$ i/n | 2.73 | 2.76 | 2.7 | 2.73 | 2.81 |
| $C_7$ i/n | 3.01 | 3.07 | 3.02 | 3.06 | 3.1 |
| $C_8$ i/n | 4 | 4.01 | 3.93 | 4 | 4.05 |
| $C_9$ i/n | 5.35 | 5.27 | 5.06 | 5.28 | 5.32 |
| $C_{10}$ i/n | 6.19 | 5.88 | 17.39 | 47.42 | 16.6 |
| $C_{11}$ i/n | 5.51 | 5.27 | 4.91 | 5.23 | 5.56 |
| $C_{12}$ i/n | 5.75 | 5.12 | 4.37 | 4.63 | 4.77 |
| $C_{13}$ i/n | 4.64 | 3.93 | 3.05 | 2.92 | 3.41 |
| $C_4$-$C_{13}$ i/n | 4.12 | 4.05 | 3.93 | 4.11 | 4.16 |
| Wt % product | | | | | |
| $C_1$-$C_3$ | <1 | <1 | <1 | <1 | <1 |
| $C_4$-$C_6$ | <10 | <10 | <10 | <10 | <10 |
| $C_7$-$C_{13}$ | 19.59 | 16.65 | 12.07 | 13.44 | 14.52 |
| i$C_{16}$ | 71.06 | 75.61 | 82.56 | 80.63 | 78.96 |
| Unidentified | 0 | 0 | 0 | 0 | 0 |
| Isoparaffin distribution | | | | | |
| Dimethyl $C_{14}$ | 79.6 | 74.8 | 66.3 | 69.1 | 71.3 |
| 6-,7-,8-Methyl$C_{15}$ | 7.8 | 9.8 | 13.4 | 12.3 | 11.4 |
| 5-Methyl$C_{15}$ | 3.7 | 4.5 | 6 | 5.5 | 5.1 |
| 4-Methyl$C_{15}$ | 2.9 | 3.6 | 4.7 | 4.3 | 4.1 |
| 3-Methyl$C_{15}$ | 3.2 | 3.9 | 5.1 | 4.7 | 4.3 |
| 2-Methyl$C_{15}$ | 2.8 | 3.3 | 4.5 | 4.1 | 3.8 |

What is claimed is:

1. An aluminosilicate ZSM-12 molecular sieve, characterized as polycrystalline aggregates of needle-like crystallites, and wherein each needle-like crystallite has a width in the range of about 15 nm to about 25 and a length in the range from about 60 nm to about 80 nm, with average dimensions of the crystallites of about 20 nm by about 60 nm, wherein the molecular sieve has a composition, as-synthesized and in the anhydrous state, in terms of mole ratios, as follows:

| | |
|---|---|
| $SiO_2/Al_2O_3$ | 30-100 |
| $(Q + A)/SiO_2$ | 0.015-0.06 |
| $M/SiO_2$ | 0-0.1 | wherein:
(1) M is at least one element selected from Groups 1 and 2 of the Periodic Table;
(2) Q is cationic 1,6-bis(2,3-dimethylimidazolium)hexane, and Q>0; and
(3) A is a second nitrogen-containing structure directing agent, and A is greater than 0;

the aluminosilicate ZSM-12 molecular sieve having an X-ray diffraction pattern substantially as shown in the following Table:

| 2 Theta | d-spacing (Angstroms) | Relative Intensity |
|---|---|---|
| 7.51 ± 0.25 | 11.76 | M |
| 8.86 ± 0.25 | 9.98 | W |
| 14.81 ± 0.25 | 5.98 | W |
| 15.28 ± 0.25 | 5.80 | W |
| 18.75 ± 0.25 | 4.73 | W |
| 19.11 ± 0.25 | 4.64 | W |
| 20.03 ± 0.25 | 4.43 | W |
| 20.91 ± 0.25 | 4.25 | VS |
| 21.98 ± 0.25 | 4.04 | W |
| 22.42 ± 0.25 | 3.96 | W |
| 22.98 ± 0.25 | 3.88 | W |
| 23.24 ± 0.25 | 3.82 | M |
| 25.21 ± 0.25 | 3.53 | W |
| 25.78 ± 0.25 | 3.45 | W |
| 26.33 ± 0.25 | 3.38 | W |
| 26.86 ± 0.25 | 3.32 | W |
| 27.99 ± 0.25 | 3.19 | W |
| 29.33 ± 0.25 | 3.04 | W |
| 30.88 ± 0.25 | 2.89 | W |
| 35.71 ± 0.25 | 2.51 | W |
| 36.97 ± 0.25 | 2.43 | W |
| 38.57 ± 0.25 | 2.33 | W. |

2. The aluminosilicate ZSM-12 molecular sieve according to claim 1, wherein the $SiO_2/Al_2O_3$ mole ratio of the aluminosilicate ZSM-12 is in the range from 30 to about 80.

3. The aluminosilicate ZSM-12 molecular sieve according to claim 1, wherein the $SiO_2/Al_2O_3$ mole ratio of the aluminosilicate ZSM-12 is in the range from 30 to about 60.

4. A method for preparing aluminosilicate ZSM-12, comprising contacting, under crystallization conditions: (1) at least one source of silicon oxide; (2) at least one source of aluminum oxide; (3) at least one source of an element selected from Groups 1 and 2 of the Periodic Table; (4) hydroxide ions; and (5) 1,6-bis(2,3-dimethylimidazolium)hexane cations.

5. The method according to claim 4, wherein the aluminosilicate ZSM-12 molecular sieve is prepared from a reaction mixture comprising, in terms of mole ratios, the following:

| | |
|---|---|
| $SiO_2/Al_2O_3$ | 30-100 |
| $(Q + A)/SiO_2$ | 0.03-0.8 |
| $M/SiO_2$ | 0.05-1 |
| $OH^-/SiO_2$ | 0.1-1 |
| $H_2O/SiO_2$ | 20-80 | wherein:
(1) M is at least one element selected from Groups 1 and 2 of the Periodic Table;
(2) Q is cationic 1,6-bis(2,3-dimethylimidazolium)hexane, and Q>0; and
(3) A is a second nitrogen-containing structure directing agent, and A is greater than 0.

6. The method according to claim 4, wherein the molecular sieve has, after calcination, an X-ray diffraction pattern substantially as shown in the following Table:

| 2 Theta | d-spacing (Angstroms) | Relative Intensity |
|---|---|---|
| 7.51 ± 0.25 | 11.76 | M |
| 8.86 ± 0.25 | 9.98 | W |
| 14.81 ± 0.25 | 5.98 | W |
| 15.28 ± 0.25 | 5.80 | W |
| 18.75 ± 0.25 | 4.73 | W |
| 19.11 ± 0.25 | 4.64 | W |
| 20.03 ± 0.25 | 4.43 | W |
| 20.91 ± 0.25 | 4.25 | VS |
| 21.98 ± 0.25 | 4.04 | W |
| 22.42 ± 0.25 | 3.96 | W |
| 22.98 ± 0.25 | 3.88 | W |
| 23.24 ± 0.25 | 3.82 | M |
| 25.21 ± 0.25 | 3.53 | W |
| 25.78 ± 0.25 | 3.45 | W |

-continued

| 2 Theta | d-spacing (Angstroms) | Relative Intensity |
|---|---|---|
| 26.33 ± 0.25 | 3.38 | W |
| 26.86 ± 0.25 | 3.32 | W |
| 27.99 ± 0.25 | 3.19 | W |
| 29.33 ± 0.25 | 3.04 | W |
| 30.88 ± 0.25 | 2.89 | W |
| 35.71 ± 0.25 | 2.51 | W |
| 36.97 ± 0.25 | 2.43 | W |
| 38.57 ± 0.25 | 2.33 | W. |

7. A method for preparing aluminosilicate ZSM-12, comprising:
(a) preparing a reaction mixture containing (1) at least one source of silicon oxide; (2) at least one source of boron oxide; (3) at least one source of an element selected from Groups 1 and 2 of the Periodic Table; (4) hydroxide ions; (5) cationic 1,4-bis(trimethylammonium)butane or cationic 1,4-bis(N-methylpiperidinium)butane as the structure directing agent; and (6) water;
(b) maintaining the reaction mixture under crystallization conditions sufficient to form crystals of borosilicate ZSM-12; and
(c) replacing boron in the framework of the borosilicate ZSM-12 with aluminum to provide aluminosilicate ZSM-12.

8. The method according to claim 7, wherein the borosilicate ZSM-12 molecular sieve is prepared from a reaction mixture comprising, in terms of mole ratios, the following:

| | |
|---|---|
| $SiO_2/B_2O_3$ | 10-100 |
| $X/SiO_2$ | 0.05-1 |
| $M/SiO_2$ | 0.1-1 |
| $OH^-/SiO_2$ | 0.1-0.6 |
| $H_2O/SiO_2$ | 20-100 | wherein M is at least one element selected from Groups 1 and 2 of the Periodic Table, and X is cationic 1,4-bis(trimethylammonium)butane or cationic 1,4-bis(N-methylpiperidinium)butane.

9. The aluminosilicate ZSM-12 molecular sieve according to claim 1, wherein A is selected from the group consisting of tetraalkylammonium cations, cationic dimethylpyrrolidinium, cationic dimethylpiperidinium, cationic dimethylpyridinium, and mixtures thereof 10. The aluminosilicate ZSM-12 molecular sieve according to claim 9, wherein A is a tetraalkylammonium cation.

11. The aluminosilicate ZSM-12 molecular sieve according to claim 10, wherein the tetraalkylammonium cation is a methyltriethylammonium cation.

12. The aluminosilicate ZSM-12 molecular sieve according to claim 10, wherein the tetraalkylammonium cation is a tetraethylammonium cation.

* * * * *